United States Patent
Fedorov et al.

(10) Patent No.: US 6,201,036 B1
(45) Date of Patent: Mar. 13, 2001

(54) LIGHT-CURABLE POLYMER MATERIAL, METHOD FOR MAKING AN ELASTIC INTRAOCULAR LENS, AND AN ELASTIC INTRAOCULAR LENS

(75) Inventors: Svyatoslav Nikolaevich Fedorov; Leonid Feodosievich Linnik, both of Moscow; Valery Mikhailovich Treushnikov; Elena Alexandrovna Viktorova, both of Nizhny Novgorod; Alexandr Alexandrovich Karavaev, Moscow, all of (RU)

(73) Assignee: Mezhoiraslevoi Nauchno-Tekhnichesky Komplex "Mikrokhirurgia Glaza", Moscow (RU)

( * ) Notice: Subject to any disclaimer, the term of this patent is extended or adjusted under 35 U.S.C. 154(b) by 0 days.

(21) Appl. No.: 09/357,484

(22) Filed: Jul. 20, 1999

(30) Foreign Application Priority Data

Jul. 21, 1998 (RU) .................................................. 98113658
Jul. 21, 1998 (RU) .................................................. 98113659
Aug. 20, 1998 (RU) .................................................. 98115813

(51) Int. Cl.$^7$ ................................. C08F 2/48; C08F 2/50; A61F 2/16; B29D 11/02
(52) U.S. Cl. ................................. 522/96; 522/44; 522/30; 522/47; 522/120; 522/121; 264/1.38; 264/2.5; 264/2.6; 264/1.36; 264/2.3; 264/1.1; 623/6; 623/6.56; 623/6.6
(58) Field of Search ................................. 623/6.56, 6.6, 623/6; 522/96, 44, 30, 47, 120, 121, 182; 264/1.38, 2.5, 2.6, 1.36, 2.3, 1.1

(56) References Cited

U.S. PATENT DOCUMENTS

| | | | |
|---|---|---|---|
| 4,110,184 | * 8/1978 | Dart et al. | 204/159.23 |
| 4,166,088 | * 8/1979 | Neefe | 264/1 |
| 4,206,518 | * 6/1980 | Jardon et al. | 3/13 |
| 4,382,902 | * 5/1983 | Feurer | 204/1.4 |
| 4,834,750 | * 5/1989 | Gupta | 623/6 |
| 4,919,850 | * 4/1990 | Blum et al. | 264/1.38 |
| 4,923,468 | * 5/1990 | Wild | 623/6 |
| 5,185,107 | * 2/1993 | Blake | 264/2.5 |
| 5,476,749 | * 12/1995 | Steinmann et al. | 430/269 |
| 5,495,029 | * 2/1996 | Stienmann et al. | 549/545 |
| 5,578,078 | * 11/1996 | Nakajima et al. | 623/6 |
| 5,725,576 | * 3/1998 | Fedorov et al. | 623/6 |
| 5,833,890 | * 11/1998 | Fedorov et al. | 264/1.38 |

* cited by examiner

Primary Examiner—James J. Seidleck
Assistant Examiner—Santa L. McClendon
(74) Attorney, Agent, or Firm—Ladas and Parry

(57) ABSTRACT

A light-curable polymer material for making an intraocular lens is a mixture of components consisting of oligourethanemethacrylate, octylmethacrylate, oligocarbonatemetharcrylate, 2,2-dimethoxy-2-phenylacetophenone and 2,4-ditretbutylortoquinone, wherein the aforesaid components are taken in the following weight % ratio:

| | |
|---|---|
| 2,2-dimethoxy-2-phenylacetophenone | 0.1–0.7 |
| 2,4-ditretbutylortoquinone | 0.001–0.006 |
| octylmethacrylate | 8–42 |
| oligocarbonatemethacrylate | 2–8 |
| oligourethanemethacrylate | balance. |

Also proposed are a method for making an elastic intraocular lens in which the aforesaid compounds are used as the initial components, and an elastic intraocular lens produced by this method.

10 Claims, 4 Drawing Sheets

LIGHT-CURABLE POLYMER MATERIAL, METHOD FOR MAKING AN ELASTIC INTRAOCULAR LENS, AND AN ELASTIC INTRAOCULAR LENS

FIELD OF THE INVENTION

The present invention relates to medicine, in particular, to ophthalmology, and more specifically to a light-curable polymer material, to a method for making an elastic intraocular lens and to an elastic intraocular lens.

BACKGROUND ART

At present intraocular lens made of polymethylmethacrylate are most widely used in ophthalmology.

Intraocular lenses of a polymer material are known (see, e.g., RF patent No. 2074673), which are made by curing a composition prepared from a mixture of oligourethanemethacrylate with the number of oxypropylene groups in the range of from 60 to 150, methylcarbitol methacrylate, methacrylic acid and 2,2-dimethoxy-2-phenylacetophenone, which are taken with the following weight % ratio of the components:

| | |
|---|---|
| 2,2-dimethoxy-2-phenylacetophenone | 0.1–0.8 |
| methacrylic acid | 2.0–10.0 |
| methylcarbitol methacrylate | 20–40 |
| oligourethanemethacrylate | balance. |

A substantial disadvantage of the polymer material is expressed by the insufficient elasticity of an intraocular lens made therefrom. Intraocular lenses from polymethylmethacrylate feature good optical characteristics and low toxicity. A drawback of these lenses is their high rigidity and hence the possibility of postoperative complications due to injury to surrounding eye tissues.

A method is known for making elastic intraocular lenses by means of high-temperature vulcanization in a casting mold of a silicone-organic polymer with subsequent thermostatic control.

It should be indicated that a prolonged holding of virtually all known polymers at high temperatures around 200–300° C. results not only in their cross-linking, but also to destruction. As a result of polymer destruction, low-molecular products are formed which are capable of diffusing into the eye tissues and causing toxic effects.

Another drawback of this method is that only a very narrow range of materials can be used to make intraocular lenses, i.e. such materials in which the shrinkage factor is close to zero. This also relates to methods for making lens, wherein curing of liquid material in a casting mold occurs under the effect of light or some other radiation. Since the shrinkage factor of the overwhelming majority of light-curable materials lies with the range of from 5 to 22%, it is considered to be impossible to use this method to make lenses having acceptable optical characteristic (see, e.g., "Polymer optic materials," Collection of papers, Chernogolovka, 1989,p. 199).

Known are U.S. Pat. No. 4,382,902 (1983) and No. 4,166,088 (1979), which teach a method for making eye contact lenses by curing a liquid material in a mold made from an optically transparent material under the effect of ultraviolet light. It should be noted that contact lenses are convexo-concave, and a considerable variation in thickness is not characteristic for such lenses. In view of this, it is conceivable that the damping devices provided in casting molds make it possible to attain satisfactory optical characteristics of the lenses.

Since an intraocular lens is biconvex or planoconvex, the variation in thickness is much greater than in contact lenses. Therefore, none of the casting mold constructions makes it possible to produce intraocular lenses having satisfactory optical characteristics, using the aforesaid method.

A method for making an elastic intraocular lens is known, wherein a liquid light-curable material is poured into a casting mold and annealing, i.e. irradiation, is carried out.

The produced intraocular lens also has insufficient elasticity, and this results in increased traumatism of the eye when an operation is performed.

It is often required that an intraocular lens have areas with more and less elasticity. A method for making intraocular lenses is known (see, e.g., RF patent No. 2074673). However, this method does not make it possible to make intraocular lenses having areas with different degrees of elasticity, either.

SUMMARY OF THE INVENTION

The object of the present invention is to create a light-curable polymer material in which the presence of a bifunctional component—oligocarbonatemethyacrylate and octylmethacrylate, makes it possible to reduce adhesion, enhance strength of the material, enhance its resilience and flexibility, and to make articles therefrom which may restore their shape after removal of a load.

Another object of the invention is to develop a method for making an elastic intraocular lens in which the use of a light-curable polymer material, including a bifunctional component—oligocarbonatemethacrylate, octylmethacrylate and an inhibitor of radical polmerization-2,4-ditretbutylortoquinone—makes it possible to make an elastic intraocular lens having reduced adhesion, enhanced strength, resilience, which is capable of being rolled into a tube and restoring its shape without deformation after the load is removed, and which also has smooth edges without roughness.

One more object of the invention is to create an elastic intraocular lens made of a light-curable polymer material including a bifunctional component—oligocarbonatemethacrylate, octylmethacrylate and an inhibitor of radical polymerization-2,4-ditretbutylortoquinone—and having reduced adhesion, enhanced strength, resilience, the capability of being rolled into a tube and restoring its shape without deformation after removal of the load, and also having smoother edges without roughness.

One more object of the invention is to create an elastic intraocular lens which combines in its construction elements having different elasticity, this making it possible to reduce traumatism of tissues during an operation.

On more object of the invention is to create an elastic intraocular lens which has high optical characteristics, no toxicity, which ensures a postoperative course without complications.

This object is achieved in that in accordance with the invention, the light-curable polymer material for making an intraocular lens is a mixture of components consisting of: oligourethanemethacrylate, having the structural formula

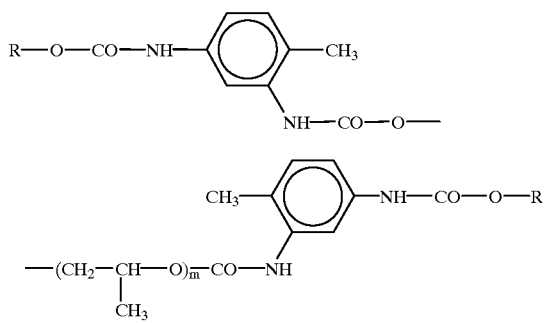

wherein: R is a radical having the formula

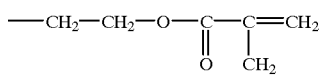

m is within the range of from 60 to 150, octylmethacrylate, having the formula

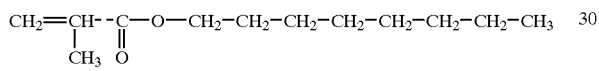

oligocarbonatemethacrylate, having the formula

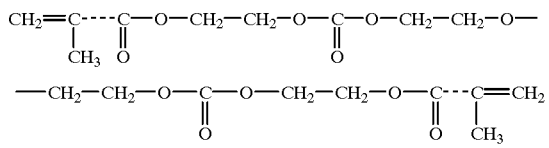

2,2-dimethoxy-2-phenylacetophenone

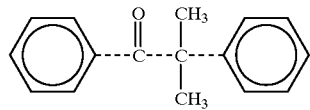

and 2,4-ditretbutylortoquinone

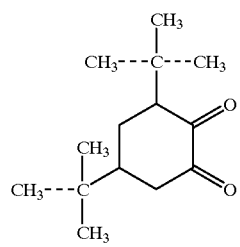

wherein the indicated components are taken in the following weight % ratios:

| | |
|---|---|
| 2,2-dimethoxy-2-phenylacetophenone | 0.1–0.7 |
| 2,4-ditretbutylortoquinone | 0.001–0.006 |
| octylmethacrylate | 8–42 |
| oligocarbonatemethacrylate | 2–8 |
| oligourethanemethacrylate | balance. |

The stated object is also achieved in that a method for making an elastic intraocular lens includes the followings steps:

using a casting mold having a base and a lid, said base and lid being made of optically transparent material, and having an annular spacer, a thickness of which is determined by the thickness of a haptic portion of the lens, said annular spacer being placed between said base and said lid, filling said base with liquid light-curable material, the base having an area for forming an optic portion of the intraocular lens, an area for forming the haptic portion of the lens, areas covered with a layer of opaque material and limited by said annular spacer, closing said base with the lid having areas covered with a layer of opaque material, an area for forming said optic portion of the intraocular lens, placed coaxially with said area for forming the optic portion of the lens on said base, by means of this forming a cell for curing said lens, pressing said lid against said base, wherewith removing an excess of said light-curable material from the curing cell, using a initial components of said light-curable material a mixture of components consisting of oligourethanemethacrylate having the structural formula

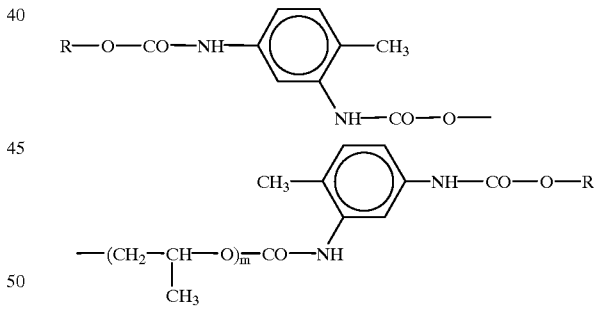

wherein: R is a radical having the formula

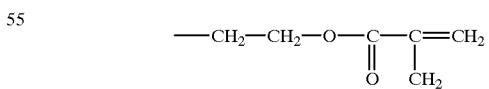

m is within the range of from 60 to 150, octylmethacrylate, having the formula

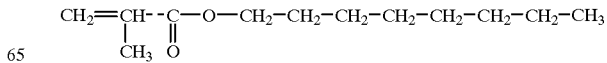

oligocarbonatemethacrylate, having the formula

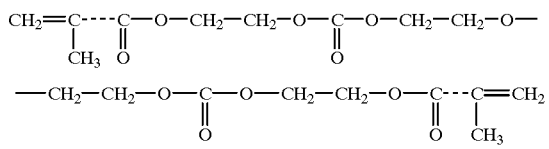

2,2-dimethoxy-2-phenylacetophenone

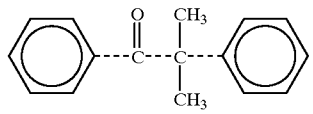

and 2,4-ditretbutylortoquinone

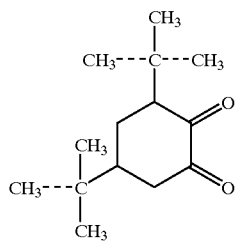

wherein the indicated components are taken in the following weight % ratios:

| | |
|---|---|
| 2,2-dimethoxy-2-phenylacetophenone | 0.1–0.7 |
| 2,4-ditretbutylortoquinone | 0.001–0.006 |
| octylmethacrylate | 8–42 |
| oligocarbonatemethacrylate | 2–8 |
| oligourethanemethacrylate | balance, | directing a focused ultraviolet light beam with a wavelength within the limits of from 320 to 380 nm along an optical axis a–a of said curing cell from the side of said lid and during irradiation of the curing cell continuously expanding the light beam from said optical axis of said cell to said edge of the area for forming the optic portion, wherein the rate of expansion of the light beam is less than the rate of curing the light-curable material, irradiating said curing cell from the side of said base with ultraviolet collimetered light having a wavelength of from 320 to 380 nm until said liquid light-curable material on areas corresponding to the haptic portion of the lens is completely cured, opening said casting mold, removing the lid, and then removing said uncured light-curable material from said areas of the base, which are covered with a layer of opaque material, and from the formed lens, placing said base with said cursed lens in an oxygen less medium at a temperature of from 40 to 60° C. and irradiating with ultraviolet light having a wavelength of from 320 to 380 nm for 3–10 minutes, placing said lens in a vessel with isopropyl alcohol at a temperature of from −20 to +12° C. and holding for from 3 to 24 hours, drying said lens in a thermal-vacuum cabinet at a temperature of from 40 to 70° C. and a residual pressure of $10^{-3}$ mmHg for from 2 to 6 hours.

It is advisable that the beam of ultraviolet light focused on said base adjacent to said optical axis on said area for forming the optic portion of the lens be directed along said optic axis of the curing cell.

It is useful that removal of the uncured said light-curable material be accomplished with an appropriate solvent.

It is also advisable that isopropyl alcohol be used as said solvent.

In another aspect, the stated object is also achieved in that the method for making an elastic intraocular lens includes the following steps:

using a casting mold having a base and a lid, said base and lid being made of optically transparent material, making an embossed pattern on said base, the height of the pattern being determined by the thickness of the haptic portion of said lens, preliminarily forming said haptic portion of said lens from a polymer fiber selected from a group consisting of polypropylene, polyimide, polyethylene, polyamide, said haptic portion including at least one haptic element, placing said haptic element in a recess of said embossed pattern so that a portion of said haptic element is placed on said area for forming the optical portion of said lens, filling the base with a liquid light-curable material, the base having an area for forming the optic portion of an intraocular lens, an area for placing said haptic element in said recess, an area for forming the haptic portion of the lens, areas covered with a layer of opaque material, closing said base with the lid, the lid having an area for forming said optic portion of the intraocular lens, said area for forming the optic portion of the intraocular lens placed coaxially with said area on the base for forming the optic portion of the lens, by means of which said cell for curing the lens is formed, pressing said lid against said base and removing an excess of light-curable material from said curing cell, using as the initial components of said light-curable material a mixture of components consisting of oligourethanemethacrylate, having the formula

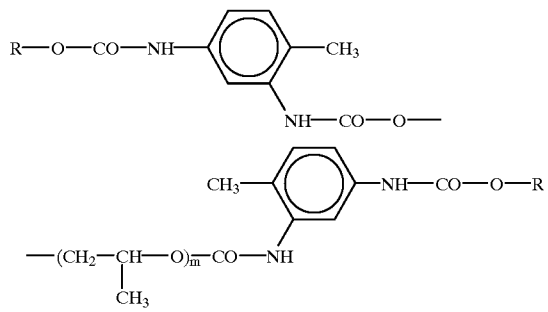

wherein: R is a radical having the formula

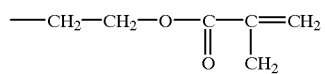

m is within the range of from 60 to 150,
octylmethacrylate, having the formula

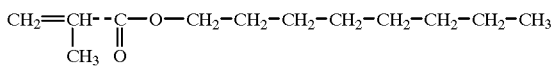

oligocarbonatemethacrylate, having the formula

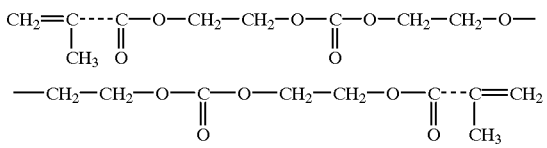

2,2-dimethoxy-2-phenylacetophenone

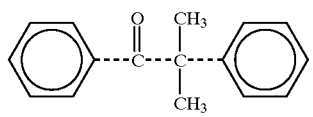

and 2,4-ditretbutylortoquinone

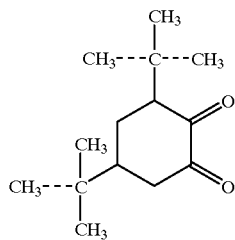

wherein the indicated components are taken in the following weight % ratios:

| | |
|---|---|
| 2,2-dimethoxy-2-phenylacetophenone | 0.1–0.7 |
| 2,4-ditretbutylortoquinone | 0.001–0.006 |
| octylmethacrylate | 8–42 |
| oligocarbonatemethacrylate | 2–8 |
| oligourethanemethacrylate | balance, | directing a focused ultraviolet light beam with a wavelength within the limits of from 320 to 380 nm along said optical axis of said curing cell from the side of said lid, and during irradiation of the curing cell continuously expanding the light beam from said optical axis of said cell to said edge of the area for forming the optic portion, wherein the rate of expansion of the light beam is less than the rate of curing the light-curable material, irradiating the curing cell from the side of the base with ultraviolet collimetered light having a wavelength of from 320 to 380 nm until said liquid light-curable material on said areas corresponding to said haptic portion of the lens is completely cured, opening said casting mold, removing said lid, and removing said uncured light-curable material from said areas of the base and said formed lens, placing said base with said cured lens in an oxygenless medium at a temperature of from 40 to 60° C. and irradiating with ultraviolet light having a wavelength of from 320 to 380 nm for 3–10 minutes, placing said lens in a vessel with isopropyl alcohol at a temperature of from −20 to +12° C. and holding for from 3 to 24 hours, drying said lens in a thermal vacuum cabinet at a temperature of from 40 to 70° C. and residual pressure of $10^{-3}$ mmHg for from 2 to 6 hours.

It is useful that removal of the uncured said light-curable material be accomplished by means of an appropriate solvent.

It is advisable that after irradiation of said cured lens with ultraviolet light having a wavelength of from 320 to 380 nm for 3–10 minutes, the obtained lens be mounted on an additional base made of a material having a high heat conduction coefficient, wherein the area of said additional base for placement of the optical portion of said lens has a diameter less than the diameter of said base, and a curvature greater than the curvature of said optic portion of said lens, said area of the base of placement of said haptic portion is made inclined at an angle α of from 1° to 15° to the horizontal plane, forming a conical surface expanding to the lower part of said additional base, closing said additional base with said lens with an additional lid made from a material from which said additional base is made, said additional lid repeating the shape of said additional base, pressing said additional lid against said additional base, creating a clearance between said additional lid and said additional base, the width of said clearance being equal to the thickness of said haptic portion of the lens, placing the prepared construction in a thermal cabinet at a temperature of from 80 to 120° C. for from 20 to 120 minutes depending on the material of said haptic portion, cooling said construction as assembled to room temperature, removing the produced lens and placing said lens in a vessel with isopropyl alcohol.

The stated object is also achieved in that an elastic intraocular lens comprises an optic portion made of light-curable polymer material on the basis of oligourethanemethacrylate, a haptic portion made from light-curable polymer material on the basis of oligourethanemethacrylate, said haptic portion forming with said optic portion a monolith construction, used as said light-curable polymer material is a mixture of components consisting of oligourethanemethacrylate having the formula

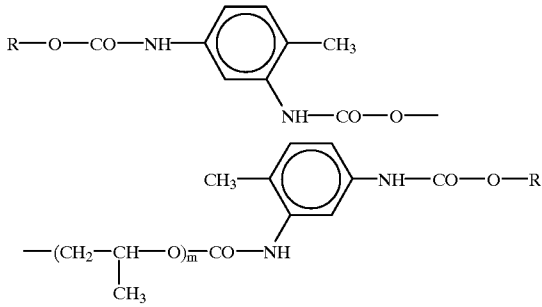

wherein: R is a radical having the formula

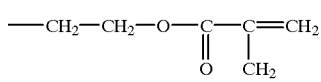

m is within the range of from 60 to 150,
octylmethacrylate, having the formula

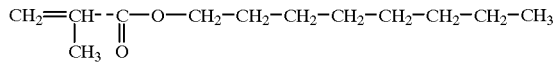

oligocarbonatemethacrylate, having the formula

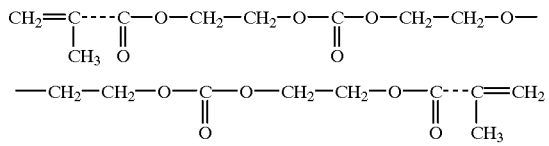

2,2-dimethoxy-2-phenylacetophenone

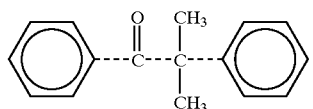

and 2,4-ditretbutylortoquinone

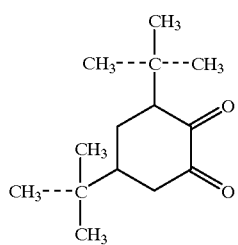

wherein the indicated components are taken in the following weight % ratios:

| | |
|---|---|
| 2,2-dimethoxy-2-phenylacetophenone | 0.1–0.7 |
| 2,4-ditretbutylortoquinone | 0.001–0.006 |
| octylmethacrylate | 8–42 |
| oligocarbonatemethacrylate | 2–8 |
| oligourethanemethacrylate | balance. |

In another aspect the stated object is also achieved in that an elastic intraocular lens comprises an optic portion made of a light-curable polymer material on the basis of oligourethanemethacrylate, a haptic portion made from a performed polymer fiber, wherein said haptic portion together with said optic portion form an integral construction, used as said light-curable polymer material is a mixture of components consisting of oligourethanemethacrylate having the formula

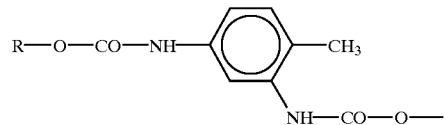

wherein: R is a radical having the formula

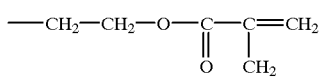

m is within the range of from 60 to 150,
octylmethacrylate, having of formula

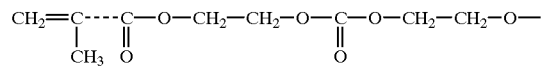

oligocarbonatemethacrylate, having the formula

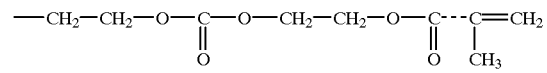

2,2-dimethoxy-2-phenylacetophenone

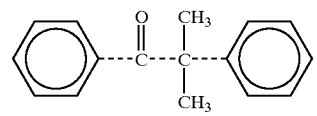

and 2,4-ditretbutylortoquinone

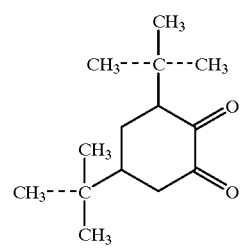

wherein the indicated components are taken in the following weight % ratios:

| | |
|---|---|
| 2,2-dimethoxy-2-phenylacetophenone | 0.1–0.7 |
| 2,4-ditretbutylortoquinone | 0.001–0.006 |
| octylmethacrylate | 8–42 |
| oligocarbonatemethacrylate | 2–8 |
| oligourethanemethacrylate | balance. |

BRIEF DESCRIPTION OF THE DRAWINGS

The invention will subsequently be explained by a description of the preferable embodiments thereof with reference to the appended drawings, wherein.

DETAILED DESCRIPTION OF THE PREFERRED EMBODIMENTS OF THE INVENTION

The light-curable polymer material for making an intraocular lens is a mixture of components consisting of oligourethanemethacrylate having the structural formula

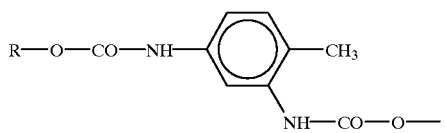

-continued

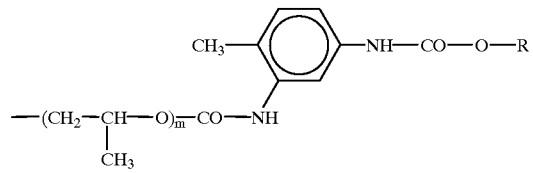

wherein: R is a radical having the formula

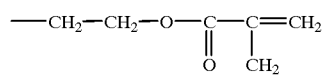

m is within the range of from 60 to 150,
octylmethyacrylate, having the formula

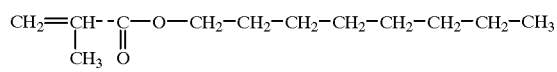

oligocarbonatemethacrylate, having the formula

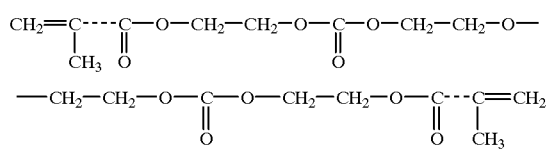

2,2-dimethoxy-2-phenylacetophenone

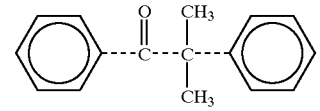

and 2,4-ditretbutylortoquinone

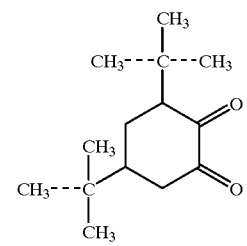

wherein the indicated components are taken in the following weight % ratios:

| | |
|---|---|
| 2,2-dimethoxy-2-phenylacetophenone | 0.1–0.7 |
| 2,4-ditretbutylortoquinone | 0.001–0.006 |
| octylmethacrylate | 8–42 |
| oligocarbonatemethacrylate | 2–8 |
| oligourethanemethacrylate | balance. |

The method for making an elastic intraocular lens is carried out in the following manner.

Figure 1:
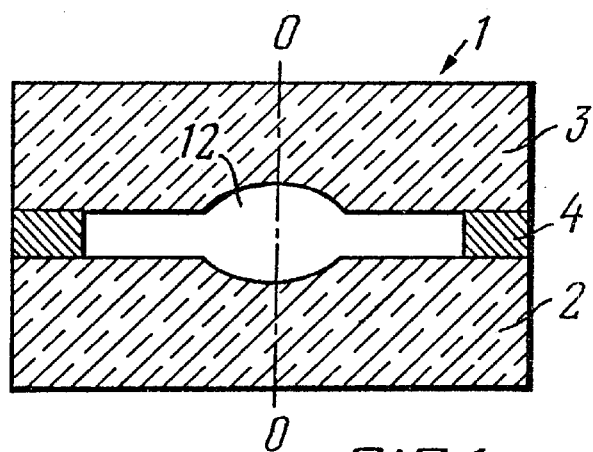
FIG. 1 shows a casting form for making a lens (longitudinal section), in accordance with the invention.

A casting mold 1 (FIG. 1) is used that has a base 2 and a lid 3, which are made of an optically transparent material, and an annular spacer 4, the thickness of which is determined by the thickness of a haptic portion of the lens. The spacer 4 is placed between the base 2 and the lid 3.

Figure 2:
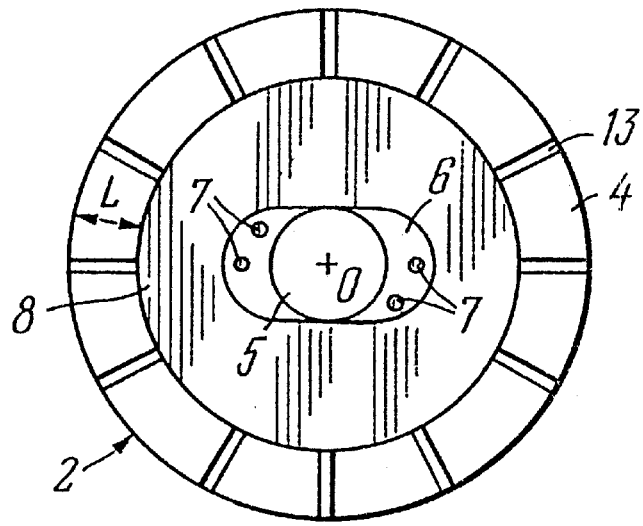
FIG. 2 shows the base of the casting mold with an annular spacer (top view), in accordance with the invention.
Figure 3:
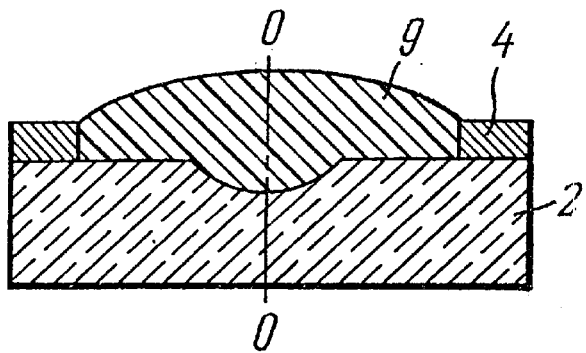
FIG. 3 shows the base with annular spacer, the base filled with a liquid light-curable material (longitudinal section), in accordance with the invention.

The base 2 (FIG. 2) comprises an area 5 for forming an optical portion of the intraocular lens, an area 6 for forming the haptic portion of the lens, areas 7, 8 covered with a layer of opaque material and limited by the annular spacer 4. The base is filled with a liquid light-curable material 9 (FIG. 3).

Figure 4:
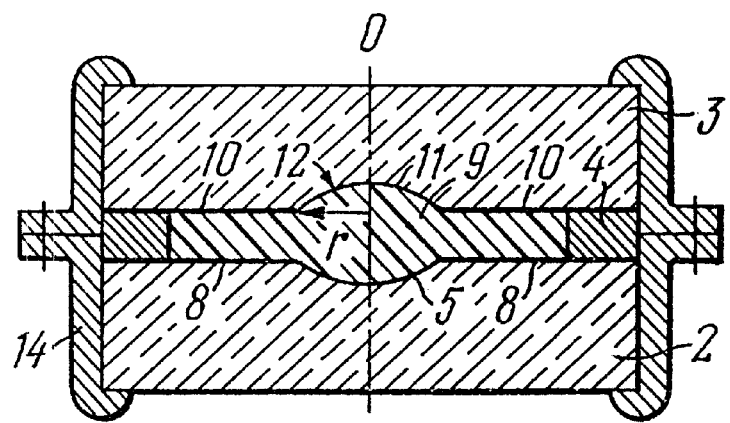
FIG. 4 shows a casting mold filled with light-curable material (longitudinal section), in accordance with the invention.

The base 2 is closed with the lid 3 (FIG. 4) which has areas 10 covered with a layer of opaque material, an area 11 for forming the optic portion of the intraocular lens, the area 11 being positioned coaxially with the area 5 on the base 2 for forming the optic portion of the lens. Wherein a cell 12 (FIG. 1) is formed for curing the lens, the cell being filled with the light-curable material 9 (FIG. 4).

The spacer 4 (FIG. 4) is a ring of metal, having a width L=2 mm and a diameter equal to the diameter of the base 2. Grooves 13 are made in the spacer 4 for removing excess light-curable material 9 from the cell.

The lid 3 is pressed (FIG. 4) against the base 2 by means of an appliance 14. Wherein the excess of light-curable material is removed from the cell 12 for curing through ducts 13 in the annular spacer 4.

Used as the initial components of said light-curable material is a mixture of components consisting of oligourethanemethacrylate having the formula

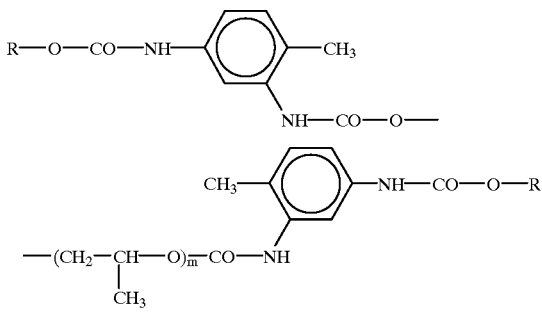

wherein: R is a radical having the formula

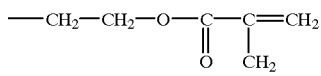

m is within the range of from 60 to 150, octylmethacrylate, having the formula

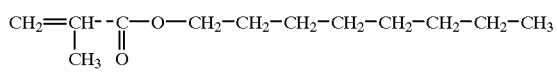

oligocarbonatemethacrylate, having the formula

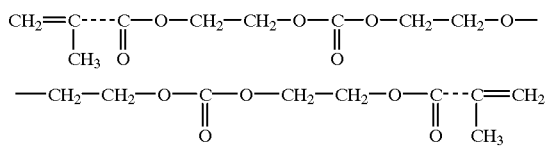

2,2-dimethoxy-2-phenylacetophenone

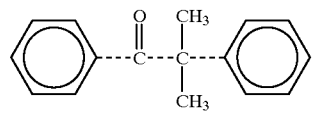

and 2,4-ditretbutylortoquinone

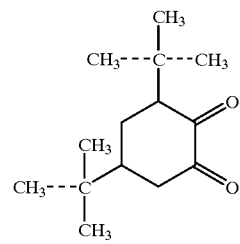

wherein the indicated components are taken in the following weight % ratios:

| | |
|---|---|
| 2,2-dimethoxy-2-phenylacetophenone | 0.1–0.7 |
| 2,4-ditretbutylortoquinone | 0.001–0.006 |
| octylmethacrylate | 8–42 |
| oligocarbonatemethacrylate | 2–8 |
| oligourethanemethacrylate | balance. |

Figure 5:
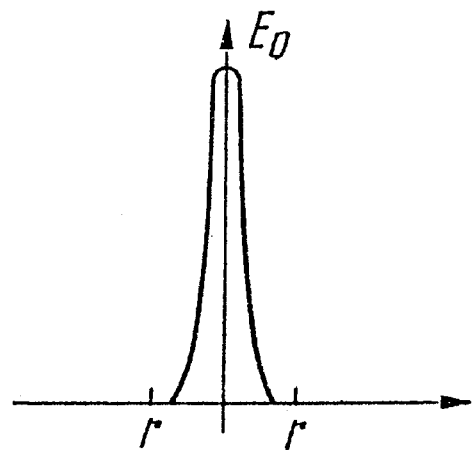
FIG. 5 shows a distribution curve of light intensity $E_o$ of the optic portion of the casting mold from the side of the lid at the initial instant of time, in accordance with the invention.

A beam of focused ultraviolet light having a wavelength within the range of from 320 to 380 nm is directed along the optical axis a—a of the curing cell 12 from the side of the lid. The distribution of the light intensity $E_o$ of the casting mold from the side of the lid in the initial instant of time along the coordinate of the radius r of the optic portion is shown in FIG. 5.

Figure 6:
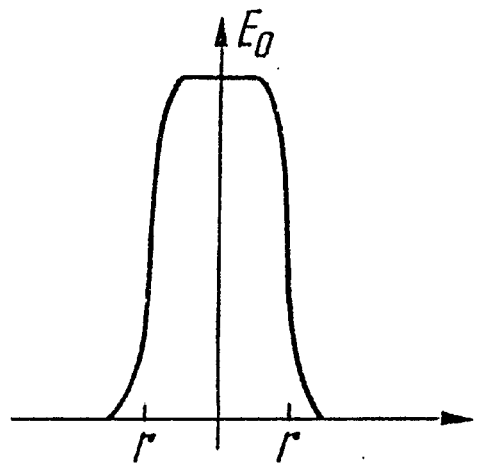
FIG. 6 shows a distribution curve of light intensity $E_o$ of the casting mold along the coordinate of the radius of the optic portion, in accordance with the invention.

Continuous expansion of the beam of light from the optical axis of the cell to the edge of an area at a distance r from the axis a—a is accomplished during irradiation of the curing cell 12 to form the optic portion. The speed of expansion of the light beam is set to be less than the speed of curing the light-curable material 9. Complete distribution of the light intensity $E_o$ along the coordinate of the radius r of the optic portion of the casting mold is shown in FIG. 6.

Then the cell 12 (FIG. 4) for curing is irradiated from the side of the base 2 with ultraviolet collimetered light having a wavelength of from 320 to 380 nm to complete curing of the liquid light-curable material 9 on the areas 6 (FIG. 2), corresponding to the haptic portion of the lens.

Figure 7:
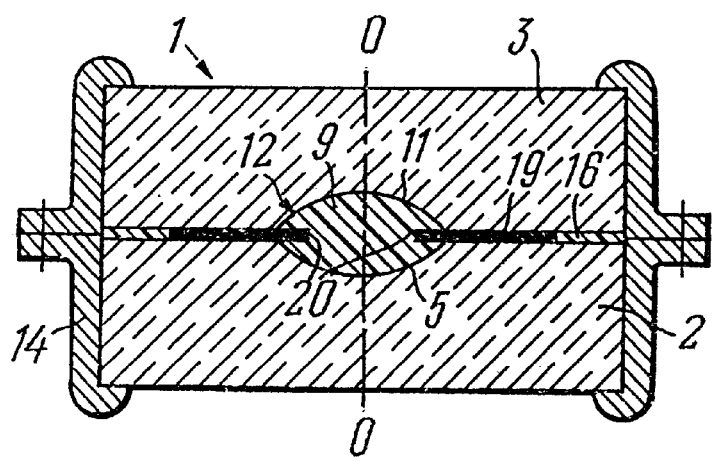
FIG. 7 shows the casting mold for making a lens with a haptic portion of polymer fiber (longitudinal section), in accordance with the invention.

The casting mold 1 (FIG. 1) is opened, the lid 3 removed, after which the uncured light-curable material is removed by means of an appropriate solvent from the areas 7, 8 (FIG. 2) of the base 2, which are covered with a layer of opaque material, and from the formed lens 15 (FIG. 7).

The base 2 with the cured lens 15 is placed in an oxygenless medium (not shown) at a temperature of from 40 to 60° C. and irradiated with ultraviolet light having a wavelength of from 320 to 380 nm for 3–10 minutes.

The lens 15 is placed in a vessel (not shown) with isopropyl alcohol at a temperature of from −20 to +12° C. and held for from 3 to 24 hours.

The lens 15 is dried in a thermal-vacuum cabinet (not shown) at a temperature of from 40 to 70° C. and residual pressure of $10^{-3}$ mmHg for from 2 to 6 hours.

A beam of ultraviolet light, focused on the base 2 adjacent the optical axis a—a on the area 5 (FIG. 4), is directed along the optical axis a—a of the curing cell 12 to form the optic portion of the lens 15.

Formation of the optic portion of the lens 15 should be accomplished from the center to the periphery in order to ensure uniform leakage of the composition during irradiation from under the opaque areas to compensate for shrinkage of the light-curable material.

Removal of the uncured light-curable material is accomplished, e.g., by using isopropyl alcohol.

A second embodiment of the method for making an elastic intraocular lens is possible, which is carried out in the following manner.

In a like manner, a casting mold 1 (FIG. 7) is used, which has a base 2 and a lid 3 that are made of optically transparent material.

Figure 8:
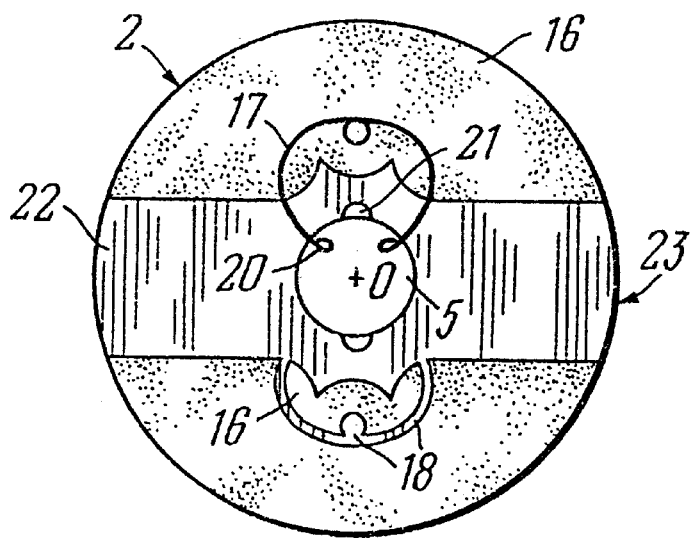
FIG. 8 shows the base of the casting mold with an embossed pattern for placement of the haptic portion of the lens (top view), in accordance with the invention.

An embossed pattern 16 is made on the base 2 (FIG. 8), the height of the pattern being determined by the thickness of a haptic portion 17 of the lens. The haptic portion 17 of the lens is placed in a slot 18 of the embossed pattern 16 on the base 2.

The haptic portion 17 of the lens is preformed of a polymer fiber selected from the group consisting of polypropylene, polyimide, polyethylene, polyamide. The haptic portion 17 includes at least one haptic element 19.

The aforesaid haptic element 19 is placed in a slot 18 of the embossed pattern 16 so that a portion 20 of the haptic element 19 is placed on the area 5 for forming the optic portion of the lens.

The base 2 is filled with a liquid light-curable material 9 (FIG. 7). The base 2 has an area 5 for forming the optic portion of the intraocular lens, a portion 18 for placement of the haptic portion 17 of polymer fiber, an area 21 for forming the haptic portion 17 of the lens, areas 22 (hatched) that are covered with a layer of opaque material (FIG. 2).

The base 2 is closed with a lid 3 which has an area 11 for forming the optic portion of the intraocular lens, the area 11 being positioned coaxially with the area 5 for forming the optic portion of the lens on the base 2, wherein the cell 12 for curing the lens is formed, which cell is filled with the light-curable material 9.

The lid 3 is pressed against the base 2 by means of a clamping device 14, wherein the excess of light-curable material 9 is removed from the curing cell 12 through a hole 23 (FIG. 8) in the embossed pattern 16.

Used as the initial components of the light-curable material is a mixture of components consisting of oligourethanemethacrylate having the formula

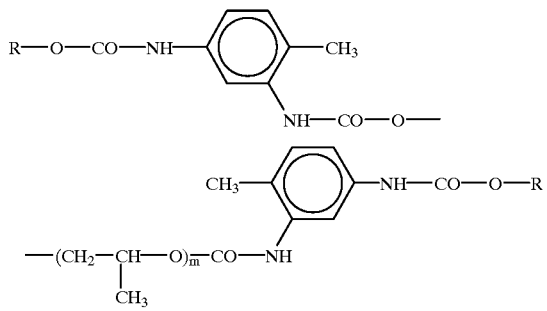

wherein: R is a radical having the formula

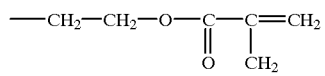

m is within the range of from 60 to 150,
octylmethacrylate, having the formula

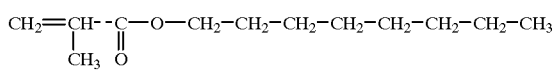

oligocarbonatemethacrylate, having the formula

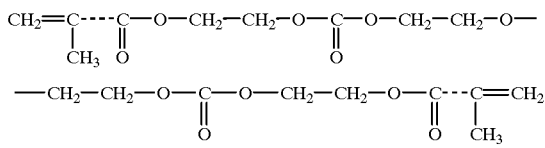

2,2-dimethoxy-2-phenylacetophenone

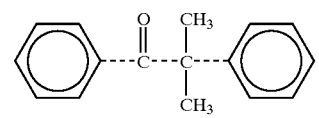

and 2,4-ditretbutylortoquinone

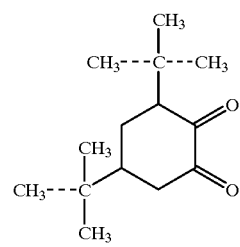

wherein the indicated components are taken in the following weight % ratios:

| | |
|---|---|
| 2,2-dimethoxy-2-phenylacetophenone | 0.1–0.7 |
| 2,4-ditretbutylortoquinone | 0.001–0.006 |
| octylmethacrylate | 8–42 |
| oligocarbonatemethacrylate | 2–8 |
| oligourethanemethacrylate | balance. |

A beam of focused ultraviolet light having a wavelength within the range of from 320 to 380 nm is directed along the optical axis a—a of the curing cell 12 from the side of the lid. The distribution of the light intensity $E_o$ of the casting mold from the side of the lid in the initial instant of time along the coordinate of the radius r of the optic portion is shown in FIG. 5.

Continuous expansion of the beam of light from the optical axis of the cell to the edge of an area at a distance r from the axis a—a is accomplished during irradiation of the curing cell 12 to form the optic portion. The rate of expansion of the light beam is set to be less than the rate of curing the light-curable material. Complete distribution of the light intensity $E_o$ of the casting mold along the coordinate of the radius r is shown in FIG. 6.

Then the cell 12 (FIG. 7) for curing is irradiated from the side of the base with ultraviolet collimetered light having a wavelength of from 320 to 380 nm until the liquid light-curable material is completely cured on the areas corresponding to the haptic portion of the lens.

The casting mold 1 is opened, the lid 3 removed, after which the uncured light-curable material is removed from areas 22 (FIG. 8) of the base, which are covered with a layer of opaque material, and from the formed lens 15.

The base 2 with the cured lens 15 is placed in an oxygenless medium (not shown) at a temperature of from 40 to 60° C. and irradiated with ultraviolet light having a wavelength of from 320 to 380 nm for 3–10 minutes.

The lens 15 is placed in a vessel (not shown) with isopropyl alcohol at a temperature of from −20 to +12° C. and held for from 3 to 24 hours.

The lens 15 is dried in a thermal-vacuum cabinet (not shown) at a temperature of from 40 to 70° C. and residual pressure of $10^{-3}$ mmHg for from 2 to 6 hours.

Removal of the uncured light-curable material is accomplished using a suitable solvent which may be isopropyl alcohol.

Figure 9A:
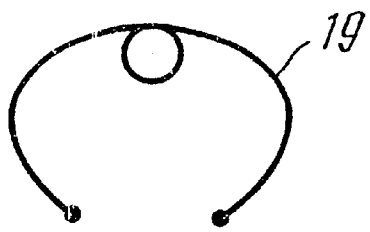
FIGS. 9a, b show the haptic element (top view), in accordance with the invention.
Figure 9B:
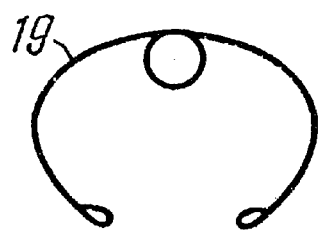

A view of the haptic element 19 is shown in FIGS. 9a and 9b. The proximal end of the haptic element 19 has an increased thickness in the form of a bead or loop, the diameters of which are greater than the thickness of the haptic element 19.

Figure 10:
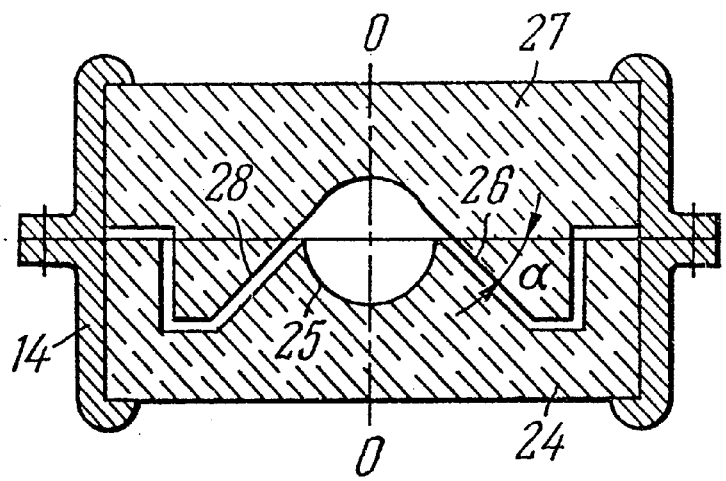
FIG. 10 shows an additional mold used for bending the haptic portion of the lends at an angle to the optic portion (longitudinal section), in accordance with the invention.

After irradiation of the cured lens 15 with ultraviolet light having a wavelength of 320–380 nm for 3–10 minutes, the obtained lens 15 is set on an additional base 24 (FIG. 10) made of a material having a high thermal conductivity coefficient. An area 25 of the additional base 24 for placement of the optic portion of the lens has a diameter less than the diameter of the first base 2, while the curvature is greater than the curvature of the optic portion of the lens 15. An area 26 for placement of the haptic portion 17 is made at an angle α of from 1 degree to 15 degrees relative to the horizontal plane, forming a conical surface which expands to the lower part of the additional base 24.

The additional base 24 with the lens 15 is closed with an additional lid 27 made of the material of the additional base 24, which lid repeats the shape of the additional base 24.

The additional lid 27 is pressed against the additional base 24, wherein a clearance 28 is created between them, the width of the clearance being equal to the thickness of the haptic portion 17 of the lens.

The obtained construction is placed in a thermal cabinet (not shown) at a temperature of from 80 to 120° C. for from 20 to 120 minutes depending on the material of the haptic portion 17.

Then the assembled construction is cooled to room temperature.

The lens 15 is removed and placed in a vessel (not shown) with isopropyl alcohol.

Figure 11:
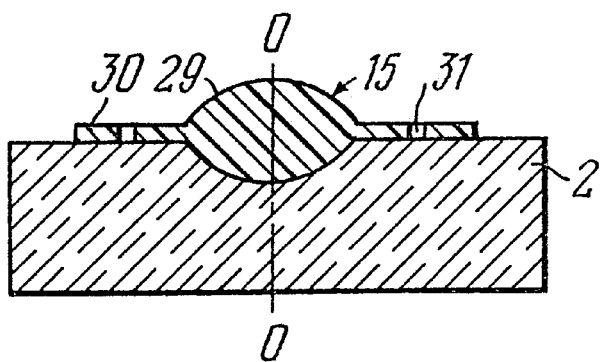
FIG. 11 shows a base with a lens positioned thereon, the lens having a monolith construction of the optic and haptic portions (longitudinal section), in accordance with the invention.

The elastic intraocular lens 15 comprises an optic portion 29 (FIG. 11) made from light-curable polymer material on the basis of oligourethanemethacrylate, a haptic portion 30 made from light-curable oligourethanemethacrylate, wherein the haptic portion 30 forms with the optic portion 29 a monolith construction. Openings 31 are made in the haptic portion 30 for rotating the lens in the eye during the operation, the geometrical dimensions of the openings 31 correspond to the geometrical dimensions of area 7 in FIG. 2.

Used as the light-curable polymer material is a mixture of components consisting of oligourethanemethacrylate having the formula

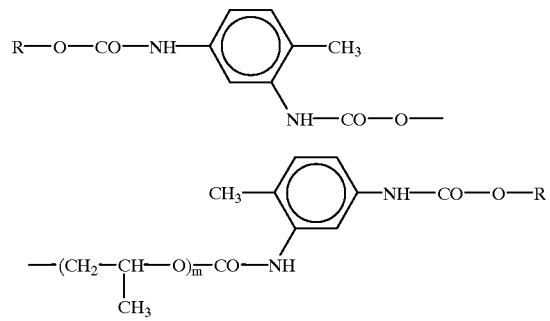

wherein: R is a radical having the formula

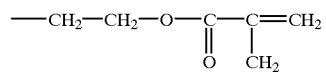

m is within the range of from 60 to 150, octylmethacrylate, having the formula

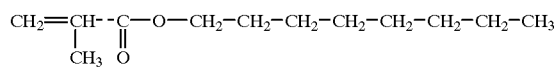

oligocarbonatemethacrylate, having the formula

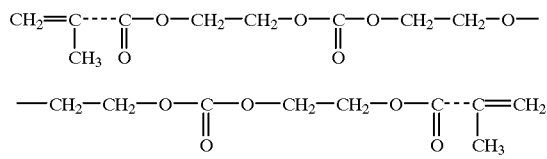

2,2-dimethoxy-2-phenylacetophenone

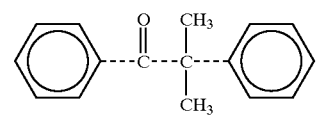

and 2,4-ditretbutylortoquinone

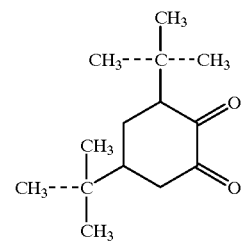

wherein the indicated components are taken in the following weight % ratios:

| | |
|---|---|
| 2,2-dimethoxy-2-phenylacetophenone | 0.1–0.7 |
| 2,4-ditretbutylortoquinone | 0.001–0.006 |
| octylmethacrylate | 8–42 |
| oligocarbonatemethacrylate | 2–8 |
| oligourethanemethacrylate | balance. |

Figure 12:
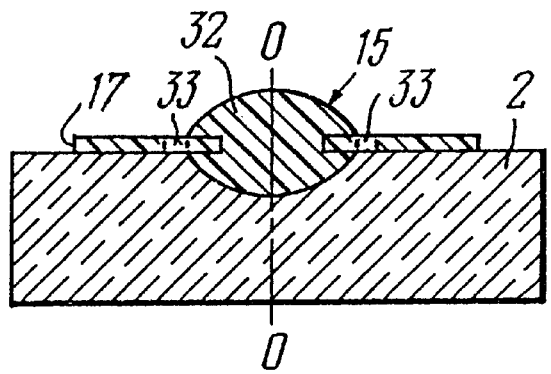
FIG. 12 shows the base with a lens positioned thereon, the lens having a monolith construction of the optic and haptic portions of a polymer fiber (longitudinal section), in accordance with the invention.

In another embodiment the elastic intraocular lens 15 comprises an optic portion 32 (FIG. 12) made of a light-curable polymer material on the basis of oligourethanemethacrylate, a haptic portion 17 made of a preformed polymer fiber, and a haptic portion 33 of the material of the optic portion, wherein the haptic portion 17 together with the optic portion 32 form an integral construction, and the haptic portion 33 with the optic portion 32 form a monolith construction.

Used as the light-curable polymer material is a mixture of components consisting of oligourethanemethacrylate having the formula

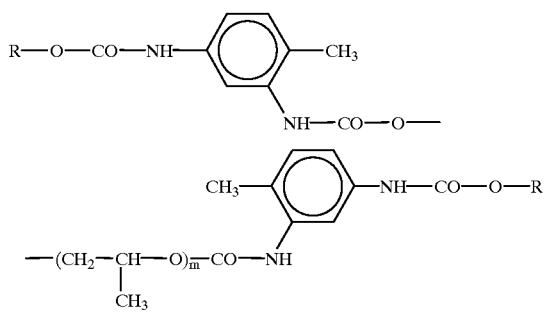

wherein: R is a radical having the formula

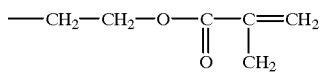

m is within the range of from 60 to 150, octylmethacrylate, having the formula

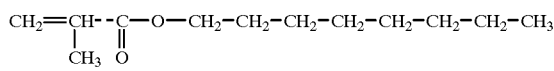

oligocarbonatemethacrylate, having the formula

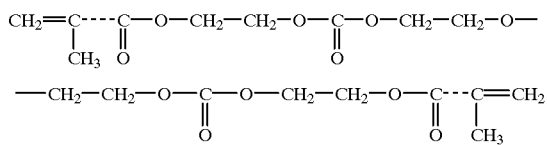

2,2-dimethoxy-2-phenylacetophenone

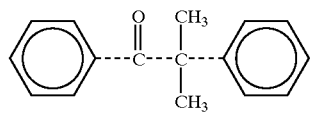

and 2,4-ditretbutylortoquinone

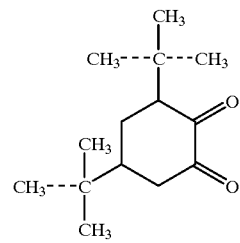

wherein the indicated components are taken in the following weight % ratios:

| | |
|---|---|
| 2,2-dimethoxy-2-phenylacetophenone | 0.1–0.7 |
| 2,4-ditretbutylortoquinone | 0.001–0.006 |
| octylmethacrylate | 8–42 |
| oligocarbonatemethacrylate | 2–8 |
| oligourethanemethacrylate | balance. |

EXAMPLE 1

The following components in the following ratio (g) were added successively to a reaction flask provided with a stirrer:

| | |
|---|---|
| oligourethanemethacrylate (R = 80) | 78.19 |
| octylmethacrylate | 13.6 |
| oligocarbonatemethacrylate | 7.58 |
| 2,2-dimethoxy-2-phenylacetophenone | 0.6265 |
| 2,4-ditretbutylortoquinone | 0.0035. |

The resultant mixture is stirred at room temperature for 40 minutes until complete dissolution of the 2,2-dimethoxy-2-phenylacetophenone and 2,4-ditretbutylortoquinone.

Once stirred the composition was filtered and pumped out with the aid of a vacuum pump at a pressure of 0.5–1 mmHg until gas evolution ceased completely.

The pumped-out composition was used for making the intraocular lens.

The lens is produced in quartz casting molds. The mold is opened and the base placed horizontally. A limiting ring of sheet polytetrafluoroethylene 150 μm thick is put on the base. Then the prepared composition is entered into recesses in the base using a 200-μl microdispenser. The base is closed with a lid and they are pressed so that the composition completely filled the whole volume between the base and the lid. Filling is carried out at room temperature, yellow light in a dustfree atmosphere. Each of the casting molds is successively placed under a microscope and at 12× magnification the edge of the optic portion of the lid is brought into coincidence with the edge of the optic portion of the base by moving the lid relative to the base. The matched up casting mold is tightly pressed and fixed.

The casting mold is carried to the exposure unit which consists of a light source (mercury-quartz lamp), a diaphragm, an optical system adapted to project the open portion of the diaphragm onto the working surface of the casting mold, and a device adapted to open the diaphragm at a preset rate.

The casting mold is so positioned in the exposure unit that an incident light ray would pass along the main optical axis of the optic portion of the casting mold, and the image of the diaphragm would from in the center of the optic portion of the base.

At the initial instant of time the diaphragm is closed. The rate of opening the diaphragm is set, which corresponds to an increase of the radius of the illuminated area of the optic portion by 3.5 mm per 7 minutes, and the first stage of exposure is carried out. The optic portion of the lens is formed during the first stage of exposure. Exposure during the second state of exposure is carried out from the side of the base.

An optimum exposure time is selected empirically. At an intensity of light incident upon the surface of the casting mold equal to 440 W/m$^2$, the optimum exposure time is 1 min 30 sec. The haptic elements of the lens are formed during the second stage of exposure.

After irradiation the casting mold is disassembled, separating the base from the lid, the ring is removed. Then all further operations are carried out with that half of the casting mold on which the formed lens remained. The base or lid is placed in a developing unit comprising a 200-ml developing dish, a developer circulating pump, and an injector provided in the dish lid. The base or lid with the lens is placed in the dish, the dish is filled with a developer (isopropyl alcohol), and the pump is turned on. The development time is 2 minutes. During the development, the unpolymerized portion of the light-curable material is removed. This unpolymerized portion during exposure was under the UV-opaque areas of the pattern. After development, the lid or base is removed, dried in a stream of warm dustfree air for 5 minutes, then is placed in an oxygenless medium at a temperature of 40–60° C. and is irradiated from a source of UV light with λ=320–380 nm, with the intensity of the light incident upon the lens surface equal to 330 W/m$^2$. After additional irradiation the lens is separated from the mold, held for from 3 to 24 hours, dried and placed in a cabinet with a temperature T=−20÷+12° C.

EXAMPLE 2

The composition is prepared as in example 1 with the following ratio of the components, g:

| | |
|---|---|
| octylmethacrylate | 8 |
| oligocarbonatemethacrylate | 2 |
| 2,2-dimethoxy-2-phenylacetophenone | 0.1 |
| 2,4-ditretbutylortoquinone | 0.001. |

The lens is made as in example 1, the characteristics are presented in Table 1.

EXAMPLE 3

The composition is prepared as in example 1 with the following ratio of the components, g:

| | |
|---|---|
| oligourethanemethacrylate (R = 80) | 49.29 |
| octylmethacrylate | 42 |
| oligocarbonatemethacrylate | 8 |
| 2,2-dimethoxy-2-phenylacetophenone | 0.7 |
| 2,4-ditretbutylortoquinone | 0.006. |

The lens is made as in example 1, the characteristics are presented in Table 1.

EXAMPLE 4

The composition is prepared as in example 1 with the following ratio of the components, g:

| | |
|---|---|
| oligourethanemethacrylate (R = 80) | 24.14 |
| octylmethacrylate | 60 |
| oligocarbonatemethacrylate | 15 |
| 2,2-dimethoxy-2-phenylacetophenone | 0.85 |
| 2,4-ditretbutylortoquinone | 0.01. |

The lens is made as in example 1, the characteristics are presented in Table 1.

EXAMPLE 5

The composition is prepared as in example 1 with the following ratio of the components, g:

| | |
|---|---|
| oligourethanemethacrylate (R = 80) | 93.9497 |
| octylmethacrylate | 5 |
| oligocarbonatemethacrylate | 1 |
| 2,2-dimethoxy-2-phenylacetophenone | 0.05 |
| 2,4-ditretbutylortoquinone | 0.0003. |

TABLE 1

| Light-curable material | Refractive index | Density g/cm$^3$ | Resolution lines/mm | Adhesion | Quality of edge |
|---|---|---|---|---|---|
| 1 | 1.4795 | 1.12 | 200 | no | smooth |
| 2 | 1.4795 | 1.12 | 200 | no | smooth |
| 3 | 1.4795 | 1.12 | 200 | no | smooth |
| 4 | 1.4760 | 1.11 | 160 | yes | rough |
| 5 | 1.4704 | 1.10 | 140 | yes | rough |

Stickiness was determined by placing the lens on silicon glass which was then turned and it was determined whether or not the lens separated therefrom under the action of its own weight. The smoothness of the edge was determined by visual examination under a microscope at 12× magnification. The remaining characteristics were determined according to the methods described in RF patent No. 2074673.

It follows from Table 1 that in examples 1, 2, 3, a lens is formed with the greatest indexes of refraction, density, resolution, with low stickiness and good quality of the edges. Deviations in respect of the formulation (examples 4 and 5) result in impairment of all of the characteristics.

The results of clinical tests which were carried out in the Institute of Microsurgery of the Eye showed that in the case of the first three examples, the postrehabilitation period is 2 days, the postoperative course was without complications, and in the case of the last two examples, the rehabilitation period was 7 days, but the postoperative course was accompanied by an inflammatory process and prolapse of the exudate.

What is claimed is:

1. A light-curable polymer material for making an intraocular lens, which is a mixture of components consisting of:

oligourethanemethacrylate, having the structural formula

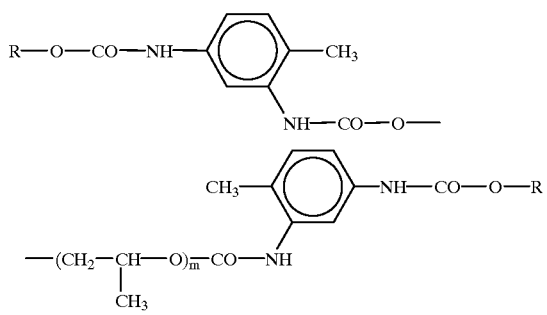

wherein: R is a radial having the formula

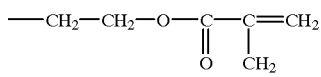

m is within the range of from 60 to 150,
octylmethacrylate, having the formula

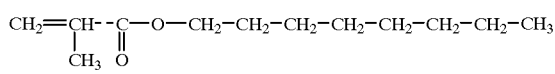

oligocarbonatemethacrylate, having the formula

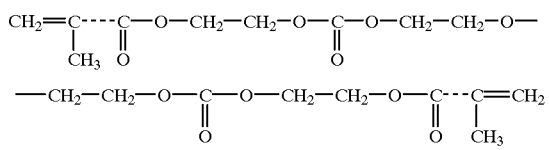

2,2-dimethoxy-2-phenylacetophenone

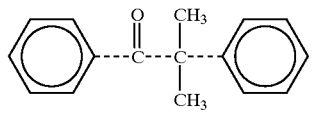

and 2,4-ditrebutylortoquinone

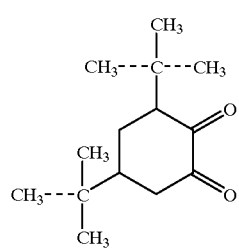

wherein the indicated components are taken in the following weight % ratios:

| | |
|---|---|
| 2,2-dimethoxy-2-phenylacetophenone | 0.1–0.7 |
| 2,4-ditretbutylortoquinone | 0.001–0.006 |
| octylmethacrylate | 8–42 |
| oligocarbonatemethacrylate | 2–8 |
| oligourethanemethacrylate | balance. |

2. A method for making an elastic intraocular lens, comprising the following steps:

using a casting mold having a base and a lid, said base and lid being made of optically transparent material, and having an annular spacer, a thickness of which is determined by the thickness of the haptic portion of the lens, said annular spacer being placed between said base and said lid, filling said base with a liquid light-curable material, the base having an area for forming an optic portion of the intraocular lens, an area for forming the haptic portion of the lens, areas covered with a layer of opaque material and limited by said annular spacer, closing said base with the lid having areas covered with a layer of opaque material, an area for forming said optic portion of the intraocular lens, placed coaxially with said area for forming the optic portion of the lens on said base, by means of this forming a cell for curing said lens, pressing said lid against said base, wherewith removing an excess of said light-curable material from the curing cell, using as initial components of said light-curable material a mixture of components consisting of oligourethanemethacrylate having the structural formula

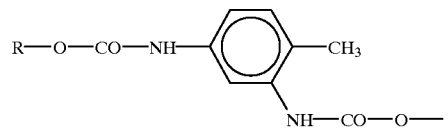

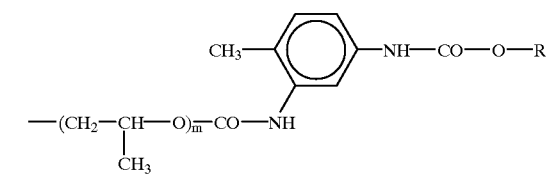

wherein: R is a radical having the formula

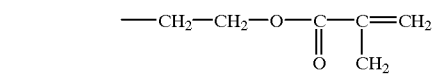

m is within the range of from 60 to 150,
octylmethacrylate, having the formula

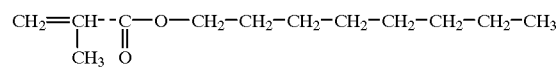

oligocarbonatemethacrylate, having the formula

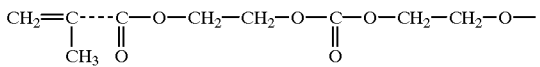

-continued

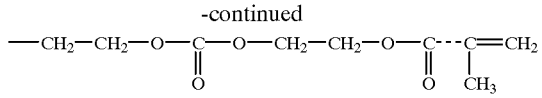

2,2-dimethoxy-2-phenylacetophenone

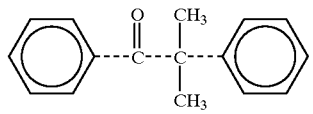

and 2,4-ditrebutylortoquinone

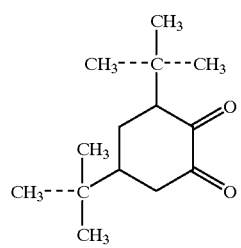

wherein the indicated components are taken in the following weight % ratios:

| | |
|---|---|
| 2,2-dimethoxy-2-phenylacetophenone | 0.1–0.7 |
| 2,4-ditretbutylortoquinone | 0.001–0.006 |
| octylmethacrylate | 8–42 |
| oligocarbonatemethacrylate | 2–8 |
| oligourethanemethacrylate | balance, | directing a focused ultraviolet light beam with a wavelength within the range of from 320 to 380 nm along an optical axis a—a of said curing cell from the side of said lid and during irradiation of the curing cell continuously expanding the light beam from said optical axis of said cell to said edge of the area for forming the optic portion, wherein the rate of expansion of the light beam is less than the rate of curing the light-curable material, irradiating said curing cell from the side of said base with ultraviolet collimetered light having a wavelength of from 320 to 380 nm until said liquid light-curable material on areas corresponding to the haptic portion of the lens is completely cured, opening said casting mold, removing the lid, and then removing said uncured light-curable material from said areas of the base which are covered with a layer of opaque material and from the formed lens, placing said base with said cured lens in an oxygenless medium at a temperature of from 40 to 60° C. and irradiating with ultraviolet light having a wavelength of from 320 to 380 nm for 3–10 minutes, placing said lens in a vessel with isopropyl alcohol at a temperature of from −20 to −12° C. and holding for from 3 to 24 hours, drying said lens in a thermal-vacuum cabinet at a temperature of from 40 to 70° C. and a residual pressure of 10 mmHg for from 2 to 6 hours.

3. A method according to claim 2, wherein the beam of ultraviolet light focused on said base adjacent to said optical axis on said area for forming the optic portion of the lens is directed along said optical axis of the curing cell.

4. A method according to claim 2, wherein removal of the uncured said light-curable material is accomplished with an appropriate solvent.

5. A method according to claim 2, wherein isopropyl alcohol is used as said solvent.

6. A method for making an elastic intraocular lens including the following steps:

using a casting mold having a base and a lid, said base and lid being made of optically transparent material, making an embossed pattern on said base, the height of the pattern being determined by the thickness of the haptic portion of said lens, preliminarily forming said haptic portion of said lens from a polymer fiber selected from a group consisting of polypropylene, polyimide, polyethylene, polyamide, said haptic portion including at least one haptic element, placing said haptic element in a recess of said embossed pattern so that a portion of said haptic element is placed on said area for forming the optic portion of said lens, filling the base with a liquid light-curable material, the base having an area for forming the optic portion of an intraocular lens, an area for placing said haptic element in said recess, an area for forming the haptic portion of the lens, areas covered with a layer of opaque material, closing said base with the lid, the lid having an area for forming said optic portion of the intraocular lens, said area for forming the optic portion of the intraocular lens placed coaxially with said area on the base for forming the optic portion of the lens, by means of which said cell for curing the lens is formed, pressing said lid against said base and removing an excess of light-curable material from said curing cell, using an the initial components of said light-curable material a mixture of components consisting of oligourethanemethacrylate, having the formula

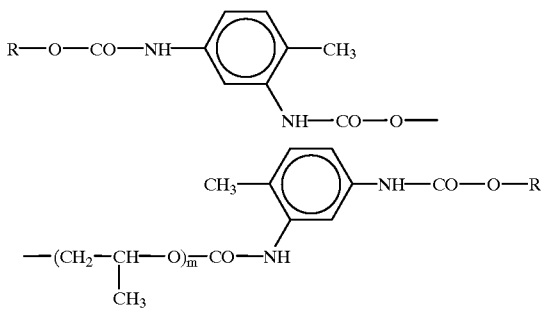

wherein: R is a radical having the formula

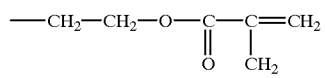

m is within the range of from 60 to 150, octylmethacrylate, having the formula

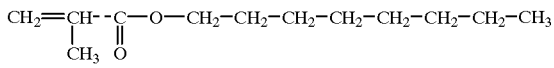

oligocarbonatemethacrylate, having the formula

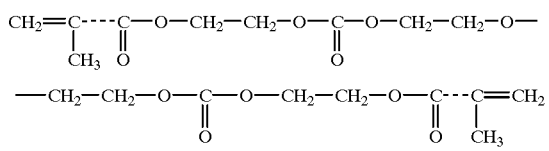

2,2-dimethoxy-2-phenylacetophenone

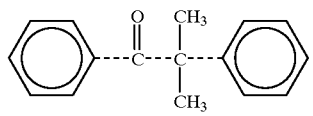

and 2,4-ditrebutylortoquinone

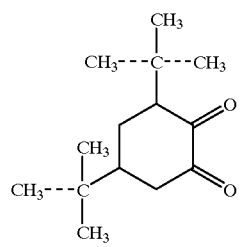

wherein the indicated components are taken in the following % ratios:

| | |
|---|---|
| 2,2-dimethoxy-2-phenylacetophenone | 0.1–0.7 |
| 2,4-ditretbutylortoquinone | 0.001–0.006 |
| octylmethacrylate | 8–42 |
| oligocarbonatemethacrylate | 2–8 |
| oligourethanemethacrylate | balance, | directing a focused ultraviolet light beam with a wavelength within the range of from 320 to 380 nm along said optical axis of said curing cell from the side of said lid, and during irradiation of the curing cell continuously expanding the light beam from said optical axis of said cell to said edge of the area for forming the optic portion, wherein the rate of expansion of the light beam is less than the rate of curing the light-curable material, irradiating the curing cell from the side of the base with ultraviolet collimetered light having a wavelength of from 320 to 380 nm until said liquid light-curable material is completely cured on said areas corresponding to said haptic portion of the lens, opening said casting mold, removing said lid, and removing said uncured light-curable material from said areas of the base and said formed lens, placing said base with said cured lens in an oxygenless medium at a temperature of from 40 to 60° C. and irradiating with ultraviolet light having a wavelength of from 320 to 380 nm for 3–10 minutes, placing said lens in a vessel with isopropyl alcohol at a temperature of from −20 to +12° C. and holding for form 3 to 24 hours, drying said lens in a thermal vacuum cabinet at a temperature of from 40 to 70° C. and residual pressure of 10 mmHg for from 2 to 6 hours.

7. A method according to claim 6, wherein removal of the uncured said light-curable material is accomplished by means of an appropriate solvent.

8. A method according to claim 6, wherein after irradiation of said cured lens with ultraviolet light having a wavelength of from 320 to 380 nm for 3–10 minutes, it further includes the following steps:

mounting the obtained lens on an additional base made of a material having a high heat conduction coefficient, wherein the area of said additional base for placement of the optic portion of said lens has a diameter less than the diameter of said base, and a curvature greater than the curvature of said optic portion of said lens, making said area of the base for placement of said haptic portion inclined at an angle α of from 1° to 15° to the horizontal plane, forming a conical surface expanding to the lower part of said additional base, closing said additional base with said lens with an additional lid made from a material from which said additional base is made, said additional lid repeating the shape of said additional base, pressing said additional lid against said additional base, creating a clearance between said additional lid and said additional base, the width of said clearance being equal to the thickness of said haptic portion of the lens, placing the prepared construction in a thermal cabinet at a temperature of from 80 to 120° C. for from 20 to 120 minutes depending on the material of said haptic portion, cooling said construction as assembled to room temperature, removing the produced lens and placing said lens in a vessel with isopropyl alcohol.

9. An elastic intraocular lens comprising an optic portion made of light-curable polymer material on the basis of oligourethanemethacrylate, a haptic portion made from light-curable polymer material on the basis of oligourethanemethacrylate, said haptic portion forming with said optic portion a monolith construction, used as said light-curable material is a mixture of components consisting of oligourethanemethacrylate having the formula

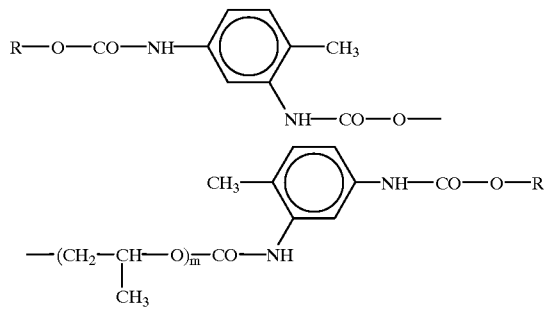

wherein: R is a radical having the formula

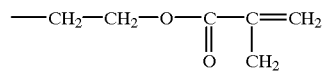

m is within the range of from 60 to 150, octylmethacrylate, having the formula $$CH_2=CH-C(CH_3)(=O)-O-CH_2-CH_2-CH_2-CH_2-CH_2-CH_2-CH_2-CH_3$$

oligocarbonatemethacrylate, having the formula $$CH_2=C(CH_3)-C(=O)-O-CH_2-CH_2-O-C(=O)-O-CH_2-CH_2-O-$$
$$-CH_2-CH_2-O-C(=O)-O-CH_2-CH_2-O-C(=O)-C(CH_3)=CH_2$$

2,2-dimethoxy-2-phenylacetophenone

[structure: diphenyl ketone with C(OCH_3)_2 group]

and 2,4-ditrebutylortoquinone

[structure: cyclohexanedione with two tert-butyl groups]

wherein the indicated components are taken in the following weight % ratios:

| | |
|---|---|
| 2,2-dimethoxy-2-phenylacetophenone | 0.1–0.7 |
| 2,4-ditretbutylortoquinone | 0.001–0.006 |
| octylmethacrylate | 8–42 |
| oligocarbonatemethacrylate | 2–8 |
| oligourethanemethacrylate | balance. |

10. An elastic intraocular lens comprising an optic portion made of a light-curable polymer material on the basis of oligourethanemethacrylate, a haptic portion made from a preformed polymer fiber, wherein said haptic portion together with said optic portion from an integral construction, used as said light-curable polymer material is a mixture of components consisting of oligourethanemethacrylate having the formula

[structure: R—O—CO—NH—(aryl with CH_3)—NH—CO—O—
and continued: CH_3—(aryl)—NH—CO—O—R with —(CH_2—CH(CH_3)—O)$_m$—CO—NH—]

wherein: R is a radical having the formula $$-CH_2-CH_2-O-C(=O)-C(CH_2)=CH_2$$

m is within the range of from 60 to 150,
octylmethacrylate, having the formula $$CH_2=CH-C(CH_3)(=O)-O-CH_2-CH_2-CH_2-CH_2-CH_2-CH_2-CH_2-CH_3$$

oligocarbonatemethacrylate, having the formula $$CH_2=C(CH_3)-C(=O)-O-CH_2-CH_2-O-C(=O)-O-CH_2-CH_2-O-$$
$$-CH_2-CH_2-O-C(=O)-O-CH_2-CH_2-O-C(=O)-C(CH_3)=CH_2$$

2,2-dimethoxy-2-phenylacetophenone

[structure: diphenyl ketone with C(OCH_3)_2 group]

and 2,4-ditrebutylortoquinone

[structure: cyclohexanedione with two tert-butyl groups]

wherein the indicated components are taken in the following weight % ratios:

| | |
|---|---|
| 2,2-dimethoxy-2-phenylacetophenone | 0.1–0.7 |
| 2,4-ditretbutylortoquinone | 0.001–0.006 |
| octylmethacrylate | 8–42 |
| oligocarbonatemethacrylate | 2–8 |
| oligourethanemethacrylate | balance. |

* * * * *

UNITED STATES PATENT AND TRADEMARK OFFICE
CERTIFICATE OF CORRECTION

PATENT NO. : 6,201,036 B1
DATED : March 13, 2001
INVENTOR(S) : Svyatoslav Nikolaevich Federov et al.

It is certified that error appears in the above-identified patent and that said Letters Patent is hereby corrected as shown below:

<u>Title page,</u>
Item [73], "Mezhoiraslevoi" should read -- Mezhotraslevoi --.

Signed and Sealed this

First Day of January, 2002

Attest:

JAMES E. ROGAN
Attesting Officer
Director of the United States Patent and Trademark Office